United States Patent [19]

Mayer et al.

[11] Patent Number: 4,973,395
[45] Date of Patent: Nov. 27, 1990

[54] HUMIDIFIED HIGH SENSITIVITY OXYGEN DETECTOR

[75] Inventors: William N. Mayer, White Bear Lake; Daniel W. Mayer, St. Paul, both of Minn.

[73] Assignee: Modern Controls, Inc., Minneapolis, Minn.

[21] Appl. No.: 437,629

[22] Filed: Nov. 17, 1989

[51] Int. Cl.$^5$ .............................................. G01N 27/26
[52] U.S. Cl. ..................................... 204/406; 204/411
[58] Field of Search ..................... 204/406, 411, 153.16

[56] References Cited

U.S. PATENT DOCUMENTS 3,223,597  12/1965  Hersch ........................... 204/153.16
4,085,024   4/1978  Lawson ...................... 204/153.16 X

OTHER PUBLICATIONS

Walter Grot, Chemie-Ing.-Techn., 47, 617, (1975).

Primary Examiner—G. L. Kaplan
Attorney, Agent, or Firm—Paul L. Sjoquist

[57] ABSTRACT

An oxygen detection device utilizing a water permeable humidifier and two galvanic cells connected in series gas flow connection, each of the galvanic cells having an anode and cathode; the respective cathodes being connected to a common connection between two load resistors, and the respective anodes being separately connected across one each of the load resistors; the device further having a third galvanic cell in close proximity to a water permeable tube to provide an oxygen getter and humidifier.

17 Claims, 3 Drawing Sheets

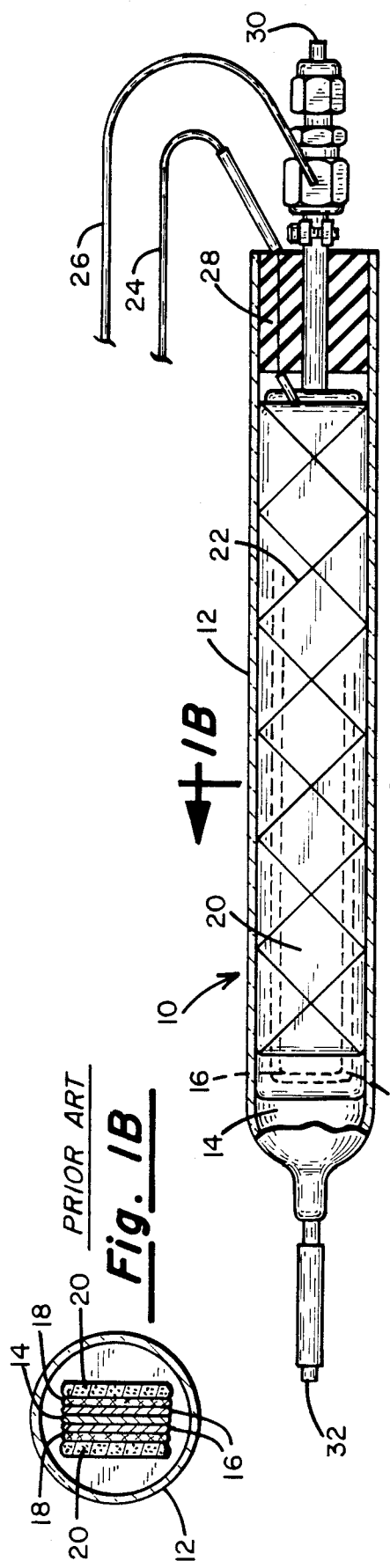
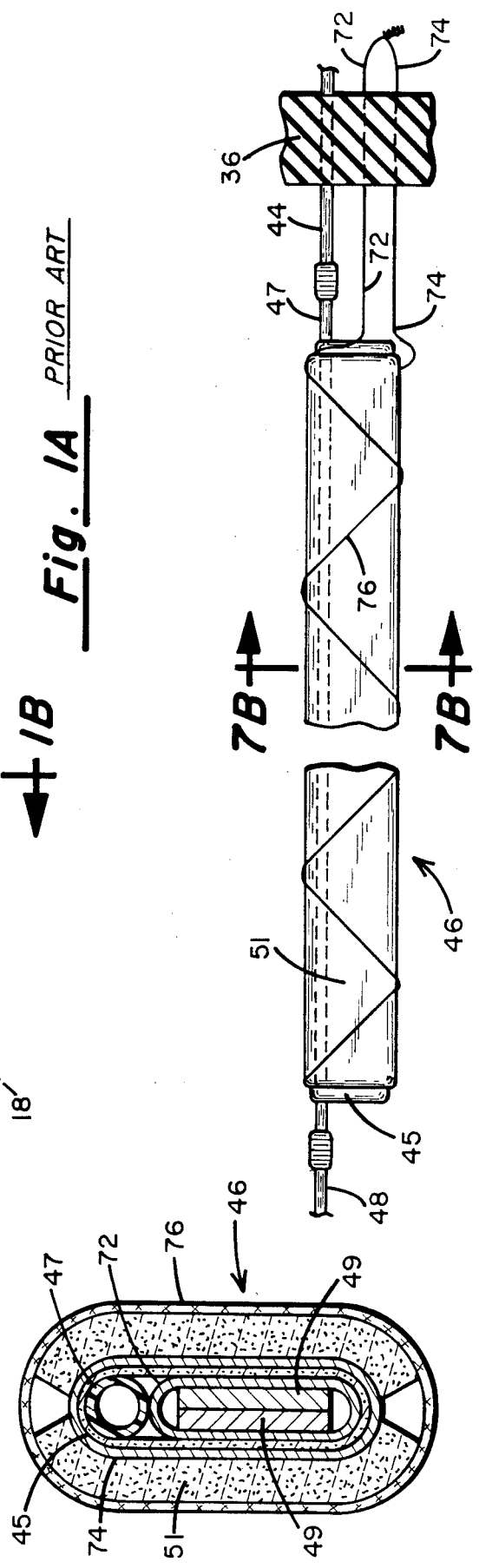
Fig. 1A PRIOR ART
Fig. 1B PRIOR ART
Fig. 7A
Fig. 7B

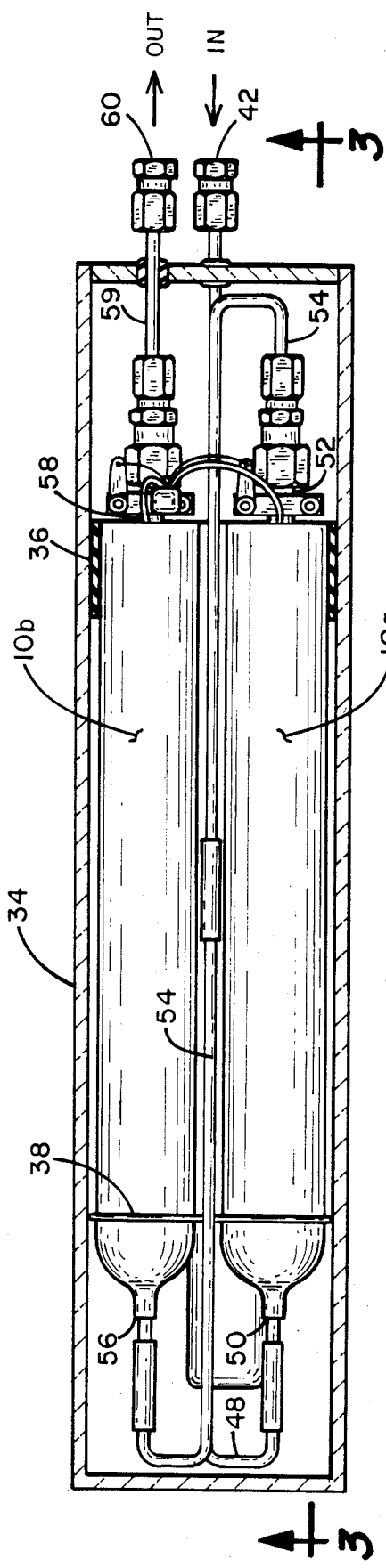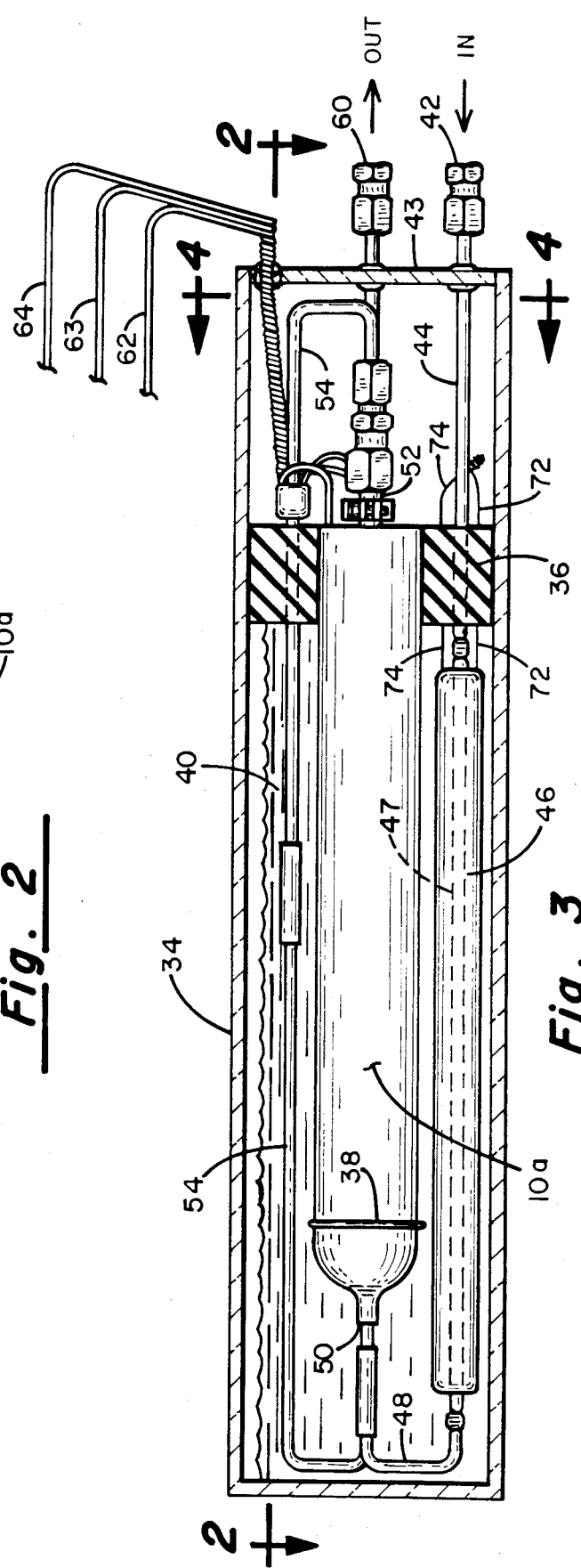

HUMIDIFIED HIGH SENSITIVITY OXYGEN DETECTOR

BACKGROUND OF THE INVENTION

The present invention relates to devices for detecting small quantities of oxygen which may be present in other gases, by the use of galvanic cells. More particularly, the invention relates to a galvanic cell oxygen detector which is capable of detecting minute quantities of oxygen in trace levels which are not detectable by prior art galvanic cell devices.

U.S. Pat. No. 3,223,597, Hersch, discloses a galvanic cell construction which includes a chemically reducing anode, a non-conductive thin porous electrolyte-retentive diaphragm in intimate contact with at least one surface of the anode, a cathode comprising a thin porous conductive sheet in intimate contact with the surface of the diaphragm opposite to the surface in contact with the anode, and an aqueous electrolyte contained in the porous diaphragm. The pores of the cathode are only partially filled with electrolyte, and the cathode is chemically nonreactive to the electrolyte, the anode being incapable of evolving hydrogen upon being circuited with the cathode. The total volume of electrolyte is less than the combined total pore volume of the cathode, diaphragm and anode, so that only a minor portion of the pores of the cathode become wetted while a major portion of the pores of the cathode never become filled. This construction results in an electrode assembly whereby only the surface of the cathode which is in intimate contact with the diaphragm is wetted, and the top surface and major portion of the pores of the cathode remain substantially dry.

U.S. Pat. No. 4,085,024, Lawson, discloses essentially the same electrode assembly as the Hersch patent, using a particular construction technique for interconnecting the elements of the cell and sealing it inside an oxygen-free envelope.

The foregoing galvanic cell constructions are critically dependent upon the concentration and quantity of electrolyte contained within the cell. Further, the sensitivity of the cell degrades with time, as the water content of the electrolyte becomes dissipated from the cell. If careful design and construction practices are followed, reliable results in detecting oxygen to about 30 parts per billion can be achieved for short periods of time, at test gas flow rates of 10-20 cubic centimeters (cc) per minute. However, this degree of accuracy is difficult to achieve because the time required for equilibrium is often longer than the time the cell remains stable.

In addition to the sensitivity variations which may be caused by varying electrolyte concentrations, there are a number of other factors which reduce the sensitivity of such galvanic cells. These variations affect the output voltage from the galvanic cell, which under idealized conditions should be directly proportional only to the oxygen content in the gas undergoing tests. For example, variations in the temperature of the device itself, or of the gas undergoing tests, will introduce output voltage variations which tend to obscure the desired output voltage signal. Further, electrochemical variations within the cell, thermal EMFs, outgasing from the wall of the cell and/or the materials within the cell, and gas pumping through the walls of the cell and/or the materials in the cell will all generate output voltage variations, which variations may be considered "noise" which obscures the desired output voltage readings. These sources of "noise" voltage may generate currents in the cell in the range of $10^{-8}$ amps per degree Centigrade change in temperature. Therefore, the prior art galvanic cells have a practical lower limit in the measurement of oxygen quantities present in the test gas, which lower limit is approximately the "noise" current generated by the cell itself.

There is a need for an oxygen sensor of the galvanic cell type which can overcome the problems of the prior art sensors, and successfully provide reliable and accurate measurements of oxygen content to a level well below about 30 parts per billion. Furthermore, there is a need for an oxygen sensor wherein sensitivity to temperature variations can be eliminated, or greatly reduced, thereby enabling the reliable use of the sensor over a wider range of environmental conditions. Finally, there is a need for an oxygen sensor having improved sensitivity over a longer useful life, being less dependent upon electrolyte concentrations in the sensor during its useful life.

SUMMARY OF THE INVENTION

The invention comprises an oxygen sensor of the galvanic cell type having a pair of galvanic cells housed within a single housing, including a test gas conduit in the housing having a water permeable section, wherein the galvanic cells are electrically connected to provide respective output voltages which may be subtractively coupled to eliminate noise signals, to thereby provide an output voltage signal which is wholly representative of oxygen content of the test gas flowing through the cell. The interior of the cell may be nearly entirely filled with electrolyte solution, to extend the useful life of the cell by way of providing an electrolyte supply far beyond the electrolyte content of prior art cells.

It is the principal object of the present invention to provide an oxygen sensor having high sensitivity over an extended useful life.

It is a further object of the present invention to provide an oxygen sensor wherein noise signals caused by temperature and other changes within the cell may be significantly reduced.

It is another object of the present invention to provide an oxygen sensor having a useful dynamic response, at least comparable with prior art sensors.

It is yet another object of the present invention to provide an oxygen sensor having the capability of detecting oxygen to levels at least several magnitudes below prior art devices.

BRIEF DESCRIPTION OF THE DRAWINGS

The foregoing and other objects and advantages of the present invention will become apparent from the following specification and claims, and with reference to the drawings, in which:

FIG. 1A shows a galvanic cell of the type known in the prior art;

FIG. 1B shows a cross-section view taken along the lines 1—1 of FIG. 1A;

FIG. 2 shows a top view of the present invention in partial cross section taken along the lines 2—2 of FIG. 3;

FIG. 3 shows an elevation view of the invention in partial cross section taken along the lines 3—3 of FIG. 2;

FIG. 7A shows a side elevation view of the humidifier of the invention; and

FIG. 7B shows a cross-section view taken along the lines 7B—7B of FIG. 7A.

DESCRIPTION OF THE PREFERRED EMBODIMENT

Figure 4:
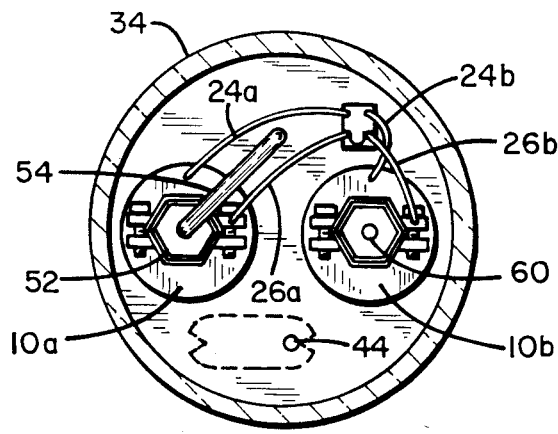
FIG. 4 shows a cross-section view taken along the lines 4—4 of FIG. 3.

Referring first to FIGS. 1A and 1B, a galvanic cell of the type known in the prior art is illustrated, in several views. Galvanic cell 10 includes a sealed gas envelope 12 which has an inlet 32 for connecting to a source of test gas, and an outlet 30 for exhausting the test gas from the cell 10. The constructional details of the elements within cell 10 may be similar to the construction described in Hersch U.S. Pat. No. 3,223,597, Lawson U.S. Pat. No. 4,085,024, or other prior art devices. The interior cell components preferably include a central anode blade 14 which is electrically coupled to an anode wire 26 which passes outside of the cell 10. Anode blade 14 has an anode element 16 adjacent each of its flat surfaces, and a porous layer 18 outwardly adjacent each of the anodes 16, and a cathode layer 20 outwardly adjacent each of the porous layers 18. The entire structure may be bound together by nylon thread 22 to form a tight assembly, and a cathode wire wrap is wound about the porous layers 18 and in electrical contact with the external cathode layers 20. The cathode wire wrap is electrically connected to a cathode wire 24 which passes outside of the cell 10. The porous layer 18 is typically impregnated with an electrolyte.

The present invention utilizes two galvanic cells of the general type described above, in a construction to be hereinafter described. The galvanic cells are hereinafter referred to as cell 10a, and cell 10b.

FIG. 2 shows a top view of the present invention in partial cross section, taken along the lines 2—2 of FIG. 3. FIG. 3 shows an elevation view of the invention in partial cross section, taken along the lines 3—3 of FIG. 2. Galvanic cells 10a and 10b are sealed within enclosure 34, by plug 36. They are supported relative to one another by a spacer 38, which also supports cells 10a and 10b relative to the inside of enclosure 34. The inside of enclosure 34 may be partially filled with an electrolyte solution 40, preferably including a 12.5 weight percentage solution of potassium hydroxide (KOH). It is desirable to nearly completely fill the sealed interior of enclosure 34 with electrolyte 40.

An inlet 42 is adapted for coupling to a source of test gas, and is coupled to a gas conduit 44 which passes through outer wall 43 of enclosure 34. Gas conduit 44 sealably passes through plug 36 and is coupled to a gas humidifier 46. Humidifier 46 has the characteristic that it is permeable to water, but includes an interior passageway through tube 47 which is a barrier to KOH; it is also chemically resistant to KOH. Humidifier 46 also contains an oxygen getter to remove any trace amounts of oxygen which may accumulate inside sealed enclosure 34, particularly in the KOH solution. A material which has been found to be suitable for the purposes required in tube 47 is Nafion. The name "Nafion" is a trademark of the E. I. Dupont de Nemours Company. The output of humidifier 46 is connected to conduit 48, which is connected to an inlet 50 of galvanic cell 10a. Galvanic cell 10a has an outlet 52 coupled to a further conduit 54 outside of the sealed portion of enclosure 34. Conduit 54 sealably passes through plug 36, and is connected to an inlet 56 of galvanic cell 10b. Galvanic cell 10b has an outlet 58 which is coupled to a conduit 59 which passes through the outer wall 43, and is connected to an outlet coupling 60, adapted for connection to an exhaust circuit.

Humidifier 46 is shown in greater detail in FIGS. 7A and 7B, wherein FIG. 7B shows a cross section of humidifier 46, taken along the lines 7B—7B of FIG. 7A. Humidifier 46 incorporates a layered structure which is arranged to form a galvanic cell, and permeable tube 47 is positioned along an anode edge of this galvanic cell. The galvanic cell may be formed of a plurality of layers of materials, in a manner similar to that described in Hersch U.S. Pat. No. 3,223,597. For example, an interior anode is comprised of two sheets of material 49 which may be made from a cadmium compound material. A metal wire 72 is tightly wrapped about the interior anode, and one end of wire 72 is brought out for subsequent connection. Permeable tube 47 is laid along an edge of anodes 49, and an intermediate porous layer 45 is wrapped about the tube 47 and anode 49. A second metal wire 74 is wrapped about porous layer 45, and one end of wire 74 is brought out for subsequent connection. Finally, an exterior cathode layer 51, which may be formed in two sections, is laid over the porous layer and a nylon wrap 76 is tightly wrapped about cathode layer 51. An end of wire 74 is electrically connected to an end of wire 72, effectively short circuiting the anode and cathode together. The electrical connection between the ends of wires 72 and 74 is made outside of enclosure 34.

Permeable tube 47 is a water permeable membrane which is chemically resistant to KOH, and which permits the controlled absorption of water into the gas flow which passes through tube 47. A material which has been found suitable for use in this purpose is a perfluorinated membrane made from a fluorocarbon copolymer of a particular chemical composition. In particular "Nafion" is a copolymer of tetraflouroethylene and a vinyl sulfonyl flouride. This membrane is sold under the trademark "Nafion," and is manufactured by E. I. Dupont de Nemours & Company.

The Nafion tube 47 is placed closely adjacent the anode 49 of humidifier 46, which serves as an oxygen getter, to reduce the oxygen in the vicinity of tube 47. Therefore, the water passing through the permeable walls of tube 47 is introduced into the test gas stream without introducing extraneous oxygen into the test gas stream. The inherent action of the galvanic cell which is formed as a part of humidifier 46 causes oxygen molecules to be absorbed into the cell, converting the cadmium anode to a cadmium hydroxide material, and therefore the oxygen is depleted from the immediate vicinity of permeable tube 47. Testing has shown that the region of lowest possible oxygen is the region immediately adjacent anode 49, and therefore tube 47 is positioned along an edge of anode 49.

Because of the characteristics of the Nafion tubing, and the concentration of KOH, the test gas which passes into the device through inlet 42 will be maintained at a constant relative humidity. The humidifier 46, including the Nafion tubing, is wholly immersed in KOH, and a dry test gas passing through the tubing in volume flow rates of approximately 20 cc/minute will inherently develop a relative humidity of about 80% (80% RH). This relative humidity will be constantly maintained throughout the passage of the gas through the galvanic cells 10a and 10b, thereby tending to replenish water which would otherwise be drawn from the device over extended periods of use. If the test gas passing into the inlet of the device has a relative humidity of greater than about 80% RH, the concentration of KOH and the permeability of the Nafion tubing will cause water to pass outwardly through the tubing, thereby depleting the humidity of the gas to about 80% RH. It can therefore be seen that the presence of the Nafion tubing immersed in a predetermined concentration of KOH tends to create a constant relative humidity under all conditions of dryness of the test gas input. This phenomena aids in the stability of oxygen test measurements, by subjecting all forms of test gas to approximately the same relative humidity during the measurement process.

Figure 5:
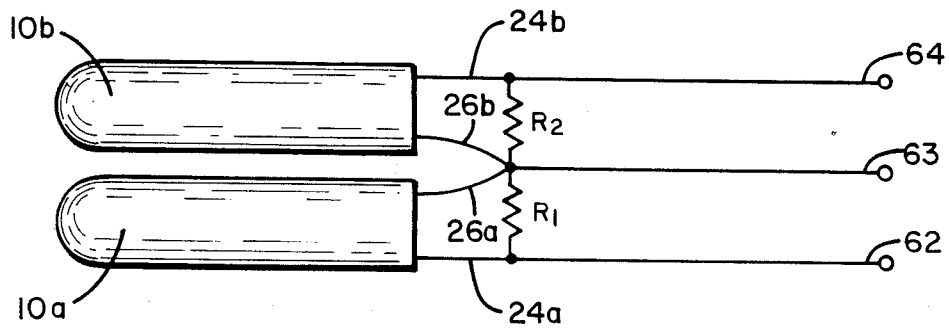
FIG. 5 shows a wiring diagram of the present invention.

FIG. 4 shows a cross-section view taken along the lines 4—4 of FIG. 3, illustrating some of the electrical and gas connections. Galvanic cell 10a has an external anode wire 26a and an external cathode wire 24a. Galvanic cell 10b has an external anode wire 26b and an external cathode wire 24b. FIG. 5 shows the connections of these wires, wherein anode wires 26a and 26b are connected together to a point intermediate resistors $R_1$ and $R_2$. Cathode wire 24a is connected to a second terminal of resistor $R_1$, and cathode wire 24b is connected to a second terminal of resistor $R_2$. These reconnection points are then brought external of enclosure 34 via common wire 63, "output 1" wire 62, and "output 2" wire 64.

It should be noted that the test gas flow path through the invention is from inlet 42, through humidifier 46, through cell 10a and then through cell 10b, and finally to outlet 60. The cathode elements of the galvanic cells 10a and 10b are electrically connected together to form a common connection, and the anode elements of the cells are each connected across a load resistance to form separate output connections.

Figure 6:
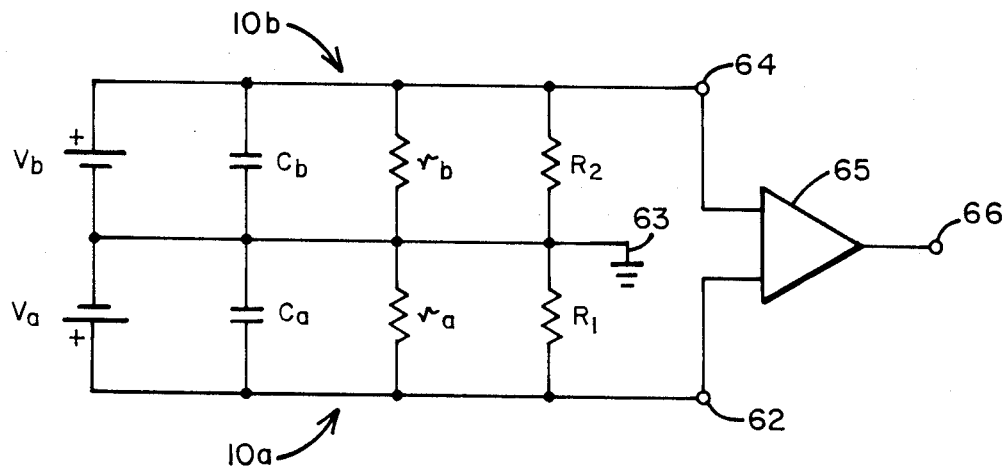
FIG. 6 shows an equivalent schematic diagram of the present invention.

FIG. 6 shows an equivalent circuit diagram which illustrates the electrical circuit formed by the invention. The galvanic action which occurs within each cell is respectively represented by $V_a$ and $V_b$; each cell has an equivalent internal capacitance $C_a$ and $C_b$; each cell has an equivalent internal resistance $r_a$ and $r_b$. The voltage developed across load resistor $R_1$ is $V_a$, which includes the galvanic voltage caused by action of the cell in detection of oxygen, and noise voltage caused by the internal cell conditions described earlier herein. Similarly, the voltage developed across load resistance $R_2$ is $V_b$, which includes the sum of the voltage developed by galvanic action of the cell in detecting oxygen plus the noise voltage developed by these same factors. However, the respective noise voltages are subtractive when the voltage is measured between terminals 62 and 64, thereby canceling out any voltage contribution traceable to noise conditions within both galvanic cells. The desired signal response to oxygen detection within the galvanic cells would also appear to be canceled out when measured between terminals 62 and 64, but for the fact that the respective galvanic cells do not equally detect the oxygen content because of their series interconnection. Because the test gas flows first through cell 10a, the oxygen molecules in the test gas are removed from the test gas by virtue of the galvanic cell action which occurs therein, therefore when the test gas is next sequentially passed through the cell 10b there is no galvanic cell action due to oxygen flow within cell 10b. In effect, cell 10b acts solely as a noise generator, generating the equivalent noise signals which are also generated in cell 10a, but these respective noise signals are then coupled in opposing voltage connection to form an output signal which subtractively removes the noise components from the useful portion of the output signal. Terminals 62 and 64 are connected to a differential amplifier 65, which may be of conventional commercial design, and amplifier 65 will produce an output signal at output terminal 66 which is representative of the test gas oxygen content.

If the values of resistances $R_1$ and $R_2$ are each selected to be 10,000 ohms (10k) and the test gas is passed through the device at a 10 cc per minute flow rate, the useful output signal will be in the microvolt range. In one test under these conditions, the total voltage measured across cell 10a (noise+useful signal) was measured at 100 microvolts, and the total voltage measured across cell 10b (noise) was measured at 75 microvolts. The voltage measured between terminal 62 and 64 was 25 microvolts, which is equivalent to an oxygen permeability measurement of 0.0025 cc per square meter per day (cc/m$^2$/day). In this case, the noise was primarily attributable to a 1° C. change in temperature which occurred during the testing interval.

With the aforementioned load resistors and test conditions, a 1 microvolt change in output voltage, measured between terminals 62 and 64, is equivalent to an oxygen permeability measurement of 0.0001 cc per square meter per day (cc/m$^2$/day); this is approximately a concentration measurement of 36 parts per trillion. Therefore, it is apparent that the present invention achieves a measurement sensitivity of at least several orders of magnitude better than the devices of the prior art. Further, the large reservoir of electrolyte contained within the device permits a constant control over relative humidity in the test gas, and replenishes water loss which otherwise would occur in the galvanic cells during extended periods of operation.

In operation, it is preferable to construct the invention with the reservoir formed by the sealed enclosure 34 nearly filled with KOH. Before actually using the completed assembly for the measurement of a test gas it is preferable to run dry nitrogen gas through the passages for a period of time in order to permit the oxygen which may be trapped inside of enclosure 34, and in solution in KOH, to be removed by the galvanic action of the cell which forms a part of humidifier 46. After an initial break-in period, which may continue for about a few days in particular applications, the device is then ready for use in measurement of the oxygen content of various test gases. The voltage output at terminal 66 may be calibrated to identify a "zero" reading after this extended break-in period, and thereafter the voltage at terminal 66 may be coupled to a circuit for driving a meter to give a direct readout of oxygen, or alternatively coupled to a circuit for conversion into digital values for processing by a computer. The device will provide accurate readings of oxygen content down to extremely low levels, and the device is usable over an extended life by virtue of the large reservoir of KOH which may be contained within enclosure 34.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. An apparatus for detecting oxygen in a test gas flow through a galvanic cell of the type which develops a current flow between a cell cathode and cell anode representative of oxygen content in the test gas, comprising:
   (a) a first galvanic cell having an inlet adapted for connection to a source of test gas, and an outlet, and having a cathode conductor and an anode conductor;
   (b) a second galvanic cell having an inlet connected to said first cell outlet, and having an outlet, and having a cathode conductor and an anode conductor;
   (c) means for commonly connecting either said respective cathode conductors or said respective anode conductors, and separately connecting the other of said respective conductors; and
   (d) a pair of load resistances having a common connection, said common connection being also connected to said respective common anode/cathode conductors, each of said load resistances being separately connected to the respective separately connected cathode/anode conductors.

2. The apparatus of claim 1, further comprising an enclosure surrounding said first and second galvanic cells.

3. The apparatus of claim 2, further comprising a reservoir in said enclosure, said reservoir being at least partially filled with an electrolyte solution.

4. The apparatus of claim 3, further comprising a test gas conduit in said reservoir, said conduit including a water-permeable section immersed in said electrolyte solution.

5. The apparatus of claim 4, wherein said water permeable section further comprises a perflourinated cation exchange polymer membrane.

6. An oxygen detection apparatus comprising:
   (a) a first galvanic cell having an anode and cathode in association with an electrolyte, confined within a first tubular bulb, said bulb having a gas inlet port and a gas outlet port;
   (b) a second galvanic cell having an anode and cathode in association with an electrolyte, confined within a second tubular bulb, said bulb having a gas inlet port and a gas outlet port;
   (c) means for coupling said first bulb gas outlet port to said second bulb gas inlet port;
   (d) means for electrically connecting together either said respective cathodes or said respective anodes to form a common connection;
   (e) a first load resistor connected between said common connection and the anode/cathode of said first cell which is not a part of said common connection; and
   (f) a second load resistor connected between said common connection and the anode/cathode of said second cell which is not a part of said common connection.

7. The apparatus of claim 6, wherein said first and second load resistors are of equal value.

8. The apparatus of claim 7, further comprising an enclosure surrounding said first and second cells, and a reservoir formed in said enclosure, said reservoir being at least partially filled with an electrolyte solution including potassium hydroxide.

9. The apparatus of claim 8, further comprising a permeable tube in said reservoir, said tube coupled to said first bulb gas inlet port and having means for externally coupling to a source of test gas; said permeable tube having the characteristic of being permeable to the passage of water therethrough.

10. The apparatus of claim 9, wherein said permeable tube further comprises a perflourinated ion exchange membrane.

11. The apparatus of claim 10, wherein said perflourinated ion exchange membrane further comprises a copolymer of tetraflouroethylene and a vinyl sulfonyl flouride.

12. An apparatus for detecting oxygen in a test gas flow through a galvanic cell of the type which develops a current flow between a cell cathode and cell anode representative of oxygen content in the test gas, comprising:
   (a) an enclosure having a reservoir at least partially filled with an electrolyte solution;
   (b) a humidifier immersed in said solution in said enclosure, said humidifier having a water permeable passage therethrough;
   (c) means for connecting a source of test gas to an inlet of said water permeable passage;
   (d) a first galvanic cell in said enclosure, said first cell having an inlet connected to said water permeable passage; and having an outlet;
   (e) a second galvanic cell in said enclosure, said second cell having an inlet connected to said first cell outlet, and having an outlet passing outside said enclosure; and
   (f) means for electrically connecting said first and second galvanic cells to provide an output signal representative of oxygen content in said test gas flow.

13. The apparatus of claim 12, wherein said humidifier further comprises a third galvanic cell having an anode and cathode electrically interconnected.

14. The apparatus of claim 13, wherein said humidifier further comprises said water permeable tube positioned closely adjacent said third galvanic cell.

15. The apparatus of claim 14, wherein said first galvanic cell further comprises a first anode and a first cathode, and said second galvanic cell further comprises a second anode and second cathode; and further comprising means for commonly connecting either said first and second anodes, or said first and second cathodes, and separately connecting the other of said respective anodes and cathodes.

16. The apparatus of claim 15, further comprising a pair of load resistances having a common connection, said common connection being also connected to said respective common anode/cathode connection, each of said load resistances being separately connected the respective separately connected anode/cathode.

17. The apparatus of claim 16, further comprising a differential amplifier having inputs respectively connected to one of said separate anode/cathode connections.

* * * * *